United States Patent [19]

Takahashi et al.

[11] Patent Number: 4,879,039

[45] Date of Patent: Nov. 7, 1989

[54] PROCESS FOR MEASURING STABLE-TYPE GLYCATED HEMOGLOBIN IN A SAMPLE

[75] Inventors: Hiroaki Takahashi, Sagamihara; Haruo Okada, Machida; Katsuya Matsumoto; Masuo Umino, both of Atsugi, all of Japan

[73] Assignee: Toyo Soda Manufacturing Co., Ltd., Shinnanyo, Japan

[21] Appl. No.: 79,435

[22] Filed: Jul. 30, 1987

[30] Foreign Application Priority Data

Jul. 30, 1986 [JP] Japan .................................. 61-177599

[51] Int. Cl.$^4$ ............................................. B01D 15/08
[52] U.S. Cl. ..................................... 210/635; 210/656; 436/67; 436/161; 436/175; 436/178; 530/385; 530/417
[58] Field of Search ...................... 530/385, 417; 436/8, 436/67, 161, 175, 178; 210/635, 656, 659

[56] References Cited

U.S. PATENT DOCUMENTS

| | | | |
|---|---|---|---|
| 3,903,254 | 9/1975 | Dahlgren | 530/385 |
| 3,914,400 | 10/1975 | Shulman | 530/385 |
| 4,243,534 | 1/1981 | Bulbenko | 436/67 |
| 4,268,270 | 5/1981 | Gabbay | 436/67 |
| 4,269,605 | 5/1981 | Dean | 436/67 |
| 4,389,491 | 6/1983 | Hanamoto et al. | 436/67 |
| 4,399,227 | 8/1983 | Niederau | 436/67 |
| 4,407,961 | 10/1983 | Sanders | 530/385 |
| 4,409,335 | 10/1983 | Hanamoto | 436/67 |
| 4,436,820 | 3/1984 | Reiter | 436/67 |
| 4,448,888 | 5/1984 | Bleile | 436/67 |
| 4,463,098 | 7/1984 | Hoberman | 436/67 |
| 4,465,774 | 8/1984 | Huang | 436/67 |

FOREIGN PATENT DOCUMENTS

| 1167278 | 5/1984 | Canada | 436/67 |
|---|---|---|---|
| WO8201804 | 5/1982 | PCT Int'l Appl. | 436/67 |

OTHER PUBLICATIONS

*Diabetologia*, (1980), Springer-Verlag, pp. 130–136, vol. 19, "Rapid Changes in Chromatographically Determined Haemoglobin $A_{1c}$ Induced by Short-Term Changes in Glucose Concentration".

*Clinical Chemistry*, vol. 28, No. 3 (1982), pp. 512–515, Nathan et al, "Rapid Method for Eliminating Labile Glycosylated Hemoglobin from the Assay for Hemoglobin $A_1$".

*Primary Examiner*—Ernest G. Therkorn
*Attorney, Agent, or Firm*—Oblon, Spivak, McClelland, Maier & Neustadt

[57] ABSTRACT

A process for measuring the amount of stable-type glycated hemoglobin in a sample using high performance liquid chromatography, comprising heating a sample diluted with a hemolysis agent containing a reagent for the removal of unstable-type glycated hemoglobin to achieve the removal of the unstable-type glycated hemoglobin, and analyzing the sample by high performance liquid chromatography.

3 Claims, 2 Drawing Sheets

PROCESS FOR MEASURING STABLE-TYPE GLYCATED HEMOGLOBIN IN A SAMPLE

BACKGROUND OF THE INVENTION

1. Field of the Invention

The present invention relates to a process for rapidly estimating the amount or presence of stable-type glycated hemoglobin in a sample, and to an apparatus for use in clinical tests to run said process.

2. Discussion of the Background

Glycated hemoglobin is produced when a saccharide in blood, mostly glucose, enters an erythrocyte and combines with hemoglobin. These saccharides enter, erythrocytes in an amount proportional to their concentration in blood.

The concentration of glycated hemoglobin in a patient reflects the mean concentration of glucose in the patient's blood through a few past months. Since the amount of glycated hemoglobin is less susceptible to physiological factors than is glucose in blood and urine, it is a more suitable index for assays used in the diagnosis of diabetes and the follow-up observation of diabetic patients.

The main component of glycated hemoglobin is a hemoglobin having attached thereto glucose at the N-terminal of the hemoglobin chain. This combination is performed in two steps involving a non-enzymatic reaction.

In the first step of the reaction the glycated hemoglobin is formed reversibly and partly decomposes to hemoglobin and saccharide. This forms so-called unstable-type glycated hemoglobin.

The second reaction is an irreversible reaction in which stable-type glycated hemoglobin is formed. A more reliable index of diabetes is obtained of course by measuring the amount of the stable-type glycated hemoglobin.

Glycated hemoglobin can be separated from hemoglobin by utilizing the differences in the electrical properties of these two materials. Methods useful for this separation include electrophoresis and ion exchange chromatography. An apparatus of high performance liquid chromatography for this particular purpose is also commercially available.

Glycated hemoglobin can be separated from ordinary hemoglobin using these methods alone, but glycated hemoglobins in their stable and unstable-types cannot be distinguished from each other. Therefore, to obtain an estimation of the stable-type glycated hemoglobin a prior treatment for the removal of the unstable-type glycated hemoglobin is required.

Prior available methods include a process in which erythrocytes are incubated in a physiological saline solution or in a buffer solution containing semicarbazide and aniline. Another process is available in which whole blood is hemolyzed in a hemolysis solution containing boric acid before incubation.

With the method which uses a physiological saline solution treatment, the erythrocytes need to be washed several times with the physiological saline solution prior to incubation, and subsequent incubation at 37° C. for more than 4 hours is required (P.A. Svensen et al., Diabetologia, 19, 130 (1980)). On the semicarbazide - aniline method involves unstable reagent solutions which need to be freshly prepared immediately before use, and subsequent incubation for 30 min to an hour at 37° C. is also required (D. M. Nathan et al., Clin. Chem., 28, 512 (1982)).

On the other hand, commercial reagents are available with which the unstable-type glycated hemoglobin can be removed. And though no problem is involved with respect to their stability, processes using these reagents require an incubation time of about 30 min at 37° C. as in the preceeding example.

All available methods suffer the inconvenience of requiring troublesome pre-treatment operations or problems preventing the rapid treatment of samples. There is therefore a strongly felt need for a new process for rapidly assaying stable-glycated hemoglobin in a patient and an apparatus for performing such a clinical test.

SUMMARY OF THE INVENTION

Accordingly, it is an object of this invention to provide a process for measuring stable-type glycated hemoglobin.

It is another object of this invention to provide a rapid process for measuring stable-type glycated hemoglobin.

It is another object of this invention to provide a process for the simple and rapid measurement of stable-type glycated hemoglobin.

It is another object of this invention to provide an apparatus for measuring stable-type glycated hemoglobin.

It is another object of this invention to provide an apparatus for rapidly measuring stable-type glycated hemoglobin.

It is another object of this invention to provide an apparatus for rapidly and simply measuring stable-glycated hemoglobin.

The inventors have now surprisingly discovered a novel process and a novel apparatus which both satisfy all the above objects of this invention, and other objects which will become apparent from a reading of the description of the invention given hereinbelow.

In the process of the present invention, stable-type glycated hemoglobin is measured by using high performance liquid chromatography. In this process, a sample diluted with a hemolysis agent containing a reagent causing the removal of unstable-type glycated hemoglobin is heated. This heating treatment achieves the removal of the unstable-type glycated hemoglobin, and the stable-type glycated hemoglobin can then be measured in the sample.

The apparatus provided by the present invention is a high performance liquid chromatography apparatus associated with a heating means. The heating means heats a sample to be analyzed by the high performance liquid chromatography apparatus before the sample is ejected into the column of the high performance liquid chromatography apparatus.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying figures.

DETAILED DESCRIPTION OF THE PREFERRED EMBODIMENTS

Figure 1:
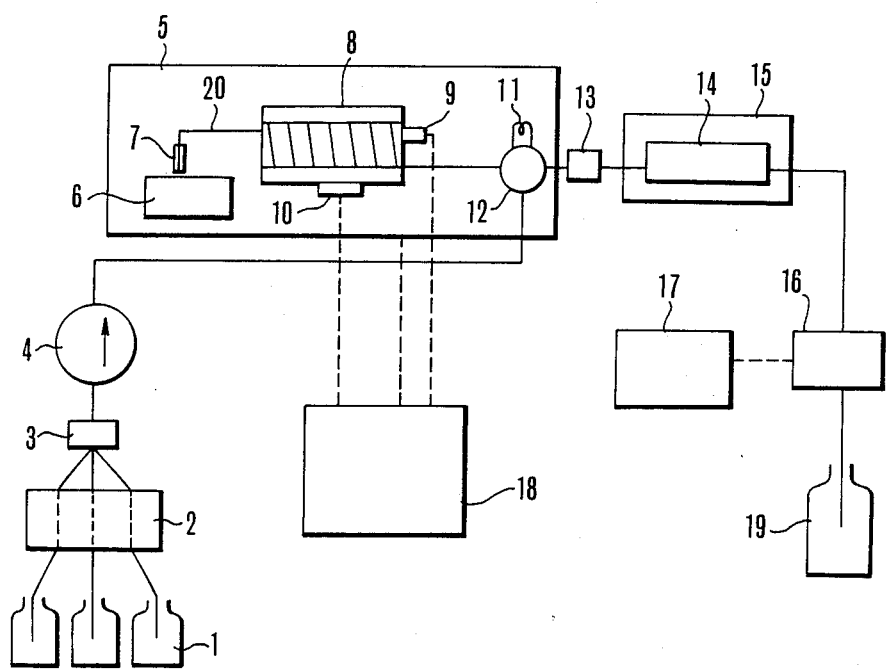
FIG. 1 provides a schematic diagram of an embodiment of the present invention, showing a measuring apparatus provided with a heating device.

The present invention provides a simpler and faster process for measuring the amount of stable-type glycated hemoglobin in a sample and an apparatus for performing this process.

More particularly, the present invention provides a process for measuring the concentration of stable-type of glycated hemoglobin in a sample. In this process a sample solution, diluted beforehand with a hemolysis solution containing a reagent which removes unstable-type glycated hemoglobin (hereinafter designated as hemolysis solution with a removing reagent), is heated to remove unstable-type glycated hemoglobin from the sample before it is introduced into a separation column of a high performance liquid chromatography instrument.

The apparatus provided by the present invention and which permits easy and rapid measurement of stabletype glycated hemoglobin in a sample by high performance liquid chromatography comprises a heating compartment for heating the sample working in association with the high performance liquid chromatography.

The reagents to be used in this invention for removing the unstable-type glycated hemoglobin include boric acid, potassium phthalate and other products generally obtained commercially for this end including surfactants and antiseptics. They may be used in mixtures of two or more, and without any further purification or pretreatment.

Hemolysis agents can also be obtained from common commercial products. Boric acid or potassium phthalate can be added as desired.

Stable-type glycated hemoglobin can be isolated by use of ion exchange chromatography. Chromatographic separation columns are packed with those cation or anion exchange resins which have been developed for the purpose, but a commercial product may also be used.

The sample solution has to be heated before it is brought to the separation column, either on-line or off-line. The on-line heating can be carried out in a variety of ways. For example, heating as a whole the table of an auto-sampler on which sample bottles are arranged, or by heating a sample vessel by an inserted heating element and heating a sucked portion of a sample solution. The last mode of heating is preferred from a point of view of heating efficiency, stability of the sample, simplicity of the apparatus and ease in performing the process. Any mode of heating may be used however, so long as the temperature of a sample solution is elevated quickly.

The temperature should be preferably in the range between 45° C. and 70° C. The higher the temperature is, the sooner the unstable-type glycated hemoglobin is removed. But at a temperature higher than 70° C. denaturation or decomposition of hemoglobin occurs in the sample and makes the separation incomplete. On the other hand, the removal of unstable-type glycated hemoglobin takes a longer time at a temperature below 45° C., and the efficacy of this invention is thus lost.

After the unstable-type glycated hemoglobin is removed by the heating treatment, the amount or presence of stable-type glycated hemoglobin in the sample is estimated from the absorbance values measured at 415 and 690 nm for the components obtained on the chromatograph.

Referring now to the Figures wherein like reference numerals designate identical or corresponding parts throughout the several views, an illustration of an example of the apparatus of this invention is provided in FIG. 1. The apparatus is a modification of a high performance liquid chromatograph. A heating device is installed between the sample suction-injection device of the autosampler and the separation column.

The apparatus of the present invention consists of a sample table 6 on which are placed samples diluted with a hemolysis agent containing a removing reagent, a suction nozzle 7 through which a sample solution is sucked, a heat block 8 for heating the sample, a sample loop 11 for measuring samples, a sample delivery device 12 with which sample and eluent solutions 1 are injected to the separation column 14 and a detector 16, and further a number of peripheral devices that are usually employed in ordinary high performance liquid chromatographs such as a degasser 2 which serves to deliver an eluent 1 to the sample delivery device 12, valves 2, a pressure pump 4, prefilter 13, a data processor and a recorder 17.

The heat block 8 is provided with a heater 9 adequately selected from a sandwich type plane heater, a plane heater with grooves and a rod heater. Heater materials are selected from those heat-conductive metals such as aluminum and copper without any particular limitation. In addition, a temperature sensor 10 and a controller 18 are provided for controlling the temperature.

Samples are first set on the sample table 6, and then sucked by the sample suction nozzle 7 in such an amount that the sample delivery tube 20 is filled up to the heat block 8. The samples are treated in the heat block 8 and then a part of the treated sample is introduced in the sample loop 11 for measurement, transferred through the sample delivery device 12 and injected into a separation column 14. The series of operations can be managed by the controller 18. Subsequently the components separated in the separation column 14 are detected by the detector 16 and determined quantitatively.

The sample delivery tube 20 extending from the sample suction nozzle 7 to the sample delivery device 12 is preferably made of a chemically resistance and thermally conductive material such as Teflon ® and stainless steel. When a Teflon ® tube is used, a tube having a small diameter and a thin wall may be desirable for the sake of high thermal effect, but practically an inner diameter 0.2 mm to 2.0 mm should be selected to maintain a small flow resistance and a sufficient mechanical strength on suction and also to reduce difficulties on manufacture.

As is evident from the above description, the present invention provides the following salient advantages:

(1) unstable-type glycated hemoglobin can be removed in a simple treatment and in a short period of time, and (2) only a very simple heating device is needed to estimate stable-type glycated hemoglobin as an index of diabetes.

Other features of the invention will become apparent in the course of the following descriptions of exemplary embodiments which are given for illustration of the invention and are not intended to be limiting thereof.

EXAMPLE 1

(A) Two blood samples were employed. One was a fresh blood sample to which sodium salt of ethylenediaminetetraacetic acid was added as anti-coagulation agent and the other was a fresh blood sample which glucose was added to (in an amount of 10 mg per ml of blood) and incubated for 30 min at 37° C., the latter being intended to produce unstable-type glycated hemoglobin in vitro.

The blood samples were diluted to 200 times as large volume with a hemolysis solution of 0.1% polyoxyether-boric acid buffer solution where boric acid is a removal reagent, and the diluted blood samples were placed on the sample table 6 as shown in FIG. 1. TSKgel Glyco (Toyo Soda Manufacturing Co., Ltd.) was placed in a separation column (4.0 id×150 mm). A temperature of 23° C. was selected for the separation.

Separation by elution was achieved with an HLC-723GHb eluent (Nippon Chemifar Co., Ltd.) with a speed of 1.6 ml/min in a stepwise gradient method at 1.1, 2.4 and 3.6 min. At the first step in the heating treatment, a 150 $\mu$ portion of a sample was sucked for each run and the sample delivery tube was a Teflon tube having an inner diameter of 0.6 mm and an outer diameter of 1/16 inch. At the heating part, each about 20 cm long Teflon ® sample delivery tube was wound around an aluminum bar heater 9 (of a 1.6 cm outer diameter and 6 cm long) and the whole was covered with an aluminum block 8.

After the heat treatment, a 20 $\mu$ portion of the resulting solution was sampled for the separation. Absorbance values at 415 and 690 (as background) were measured with the detector 16, to obtain the content of stable-type glycated hemoglobin.

Figure 2:
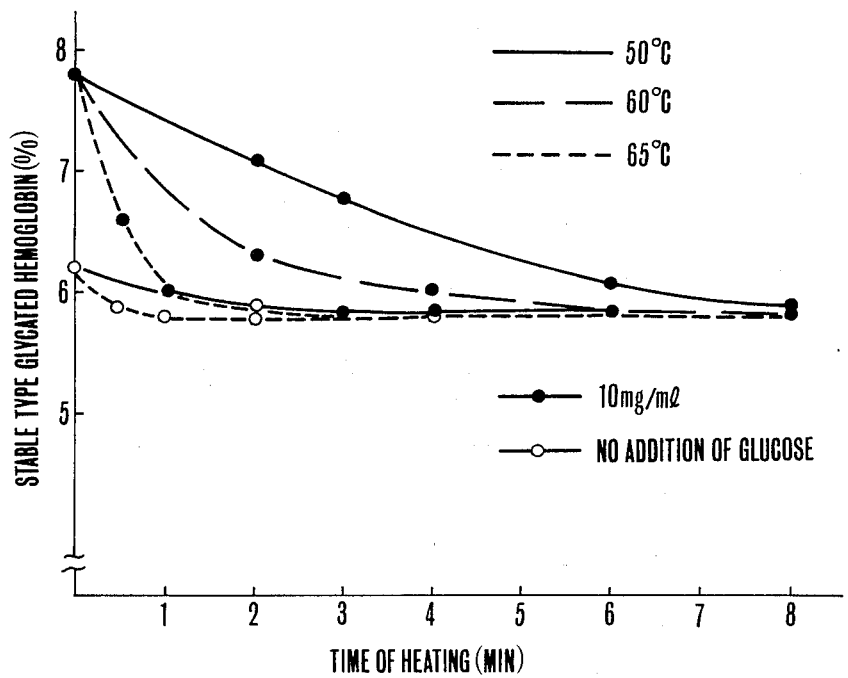
FIG. 2 graphically shows the relation between the removal of unstable-type glycated hemoglobin and the heating time at different temperatures of heating.

The efficiency with which to remove unstable-type glycated hemoglobin was estimated with the temperature and time of the heating treatment varied and the result obtained is summarized in FIG. 2. Values obtained when glucose was added and not are indicated by solid and blank circles, respectively.

Even for the samples in which unstable-type glycated hemoglobin was formed in vitro in the presence of glucose, the unstable-type glycated hemoglobin was removed in 8 min. at 50° C. and in 1 min. at 65° C. With the fresh blood samples to which glucose was not added, a 2 min. heating time sufficed even at 50° C. in contrast to more than 30 min. at 37° C. in prior arts. Thus, it proved the treatment proceeded in a particularly shorter time.

(B) Estimated values of the present invention were compared with those of previous processes which employ treatment with a physiological saline solution.

Samples used were freshly taken blood samples from normal persons and diabetic patients and an anti-coagulation reagent was added to all samples. Conditions of measurement were the same as in (A) except the temperature of the heat block and the period of heating time being 65° C. and 1.5 min., respectively.

In a pre-treatment of the physiological saline solution method, about 10 times as much physiological saline solution as the whole blood was added, agitated, centrifuged, and a supernatant liquid was discarded. After the procedure being repeated twice, about 10 times as much physiological saline solution was added and the whole mixture was incubated at 37° C. for 4 hours.

Then centrifugation followed and such an amount of excessive supernatant liquid was discarded so as to leave the same volume of supernatant liquid as that of blood corpuscles. The whole blood was diluted up to 200 times as large volume with a hemolysis agent for HLC-723GHL (consisting of 0.1% of triton X-100, 0.1% of sodium salt of ethylenediamine-tetraacetic acid and 0.1% of sodium azide) and the mixture was submitted to measurement. The procedure was carried out with an apparatus which was not provided with a heat block, but other conditions were the same as those with a heat block.

Figure 3:
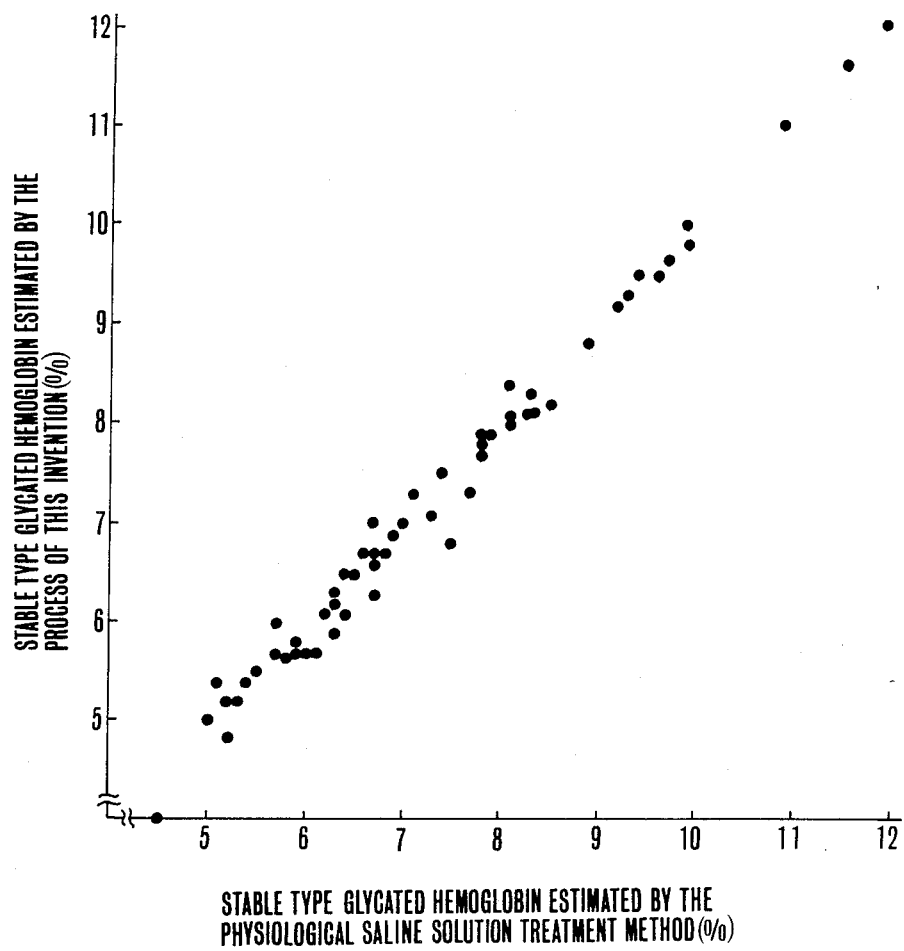
FIG. 3 shows the correlation existing between the process of this invention and a prior art process which comprises treatment with a physiological saline solution.

Result of estimations with 63 samples is shown in FIG. 3. A very high value of correlation was obtained between the processes of this invention and the physiological saline solution method with a correlation factor 0.9940. A correlation formula was derived as follows:

$$Y = 1.031X - 0.308$$

where X and Y were values obtained the present invention and the physiological saline solution method, respectively. This result demonstrated that, in this invention, unstable-type glycated hemoglobin was completely removed as in the previous process.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for measuring the amount of stable-type glycated hemoglobin in a sample using high performance liquid chromatography, comprising heating to a temperature of at least 45° C. a sample diluted with a hemolysis agent containing a reagent for the removal of unstable-type glycated hemoglobin comprising boric acid to achieve the removal of the unstable-type glycated hemoglobin, and analyzing the sample by high performance liquid chromatography.

2. The process of claim 1, comprising heating said sample to a temperature between 45° C. and 70° C.

3. The process of claim 1, wherein said sample is a sample obtained from a human patient.

* * * * *